United States Patent [19]
Schwark et al.

[11] Patent Number: 6,093,729
[45] Date of Patent: Jul. 25, 2000

[54] SUBSTITUTED BICYCLIC HETEROAROYLGUANIDINES, A PROCESS FOR THEIR PREPARATION, THEIR USE AS A MEDICAMENT OR A DIAGNOSTIC AGENT, AND A MEDICAMENT CONTAINING THEM

[75] Inventors: Jan-Robert Schwark, Frankfurt; Heinz-Werner Kleemann, Bischofsheim; Hans-Jochen Lang, Hofheim; Andreas Weichert, Egelsbach; Wolfgang Scholz, Eschborn; Udo Albus, Florstadt, all of Germany

[73] Assignee: Hoechst Aktiengesellschaft, Frankfurt am Main, Germany

[21] Appl. No.: 09/195,098

[22] Filed: Nov. 18, 1998

Related U.S. Application Data

[63] Continuation of application No. 08/968,342, Nov. 12, 1997, abandoned, which is a continuation of application No. 08/665,580, Jun. 18, 1996, abandoned, which is a continuation of application No. 08/434,249, May 3, 1995, abandoned.

Foreign Application Priority Data

May 5, 1994 [DE] Germany .............................. 44 15 873

[51] Int. Cl.⁷ ..................... C07D 215/00; C07D 217/00; A61K 31/47
[52] U.S. Cl. .......................... 514/307; 514/311; 546/139; 546/146; 546/152; 546/156
[58] Field of Search ..................... 546/146, 139, 546/152, 156; 564/180; 514/307.634, 311

[56] References Cited

U.S. PATENT DOCUMENTS

| | | | |
|---|---|---|---|
| 3,780,027 | 12/1973 | Cragoe et al. ...................... | 260/239.6 |
| 5,091,394 | 2/1992 | Englert et al. ......................... | 514/331 |
| 5,364,868 | 11/1994 | Englert et al. ......................... | 514/331 |
| 5,373,024 | 12/1994 | Lang et al. .............................. | 514/618 |
| 5,416,094 | 5/1995 | Lal et al. ................................ | 514/307 |

OTHER PUBLICATIONS

H. Lorne Davis et al., "2,3–Disubstituted 1,8–Naphthyridines as Potential Diuetic Agents. 3. 4– and 7–Phenyl Derivatives," Eur. . Med. Chem.—Chim. Ther., vol. 20, No. 4, pp. 381–383, 1985.

E.M. Hawes et al., "2–3–Disubstituted 1,8–Naphthyridines as Potential Diuretic Agents. 2. 5,7–Dimethyl Derivatives," J. Med. Chem. (JCMAR), 77, vol. 20, No. 6, pp. 838–841, 1977.

D.K.J. Gorecki et al., "2,3–Disubstituted 1,8–Naphthyridines as Potential Diuretic Agents," J. Med. Chem. (JCMAR), 77, vol. 20, No. 1, pp. 124–128, 1977.

E.M. Hawes et al., "2,3–Disubstituted 1,6–Naphthyridines as Potential Diuretic Agents," J. Med. Chem. (JCMAR), 73, vol. 16, No. 7, pp. 849–853, 1973.

Davis et al., Chemical Abstracts, vol. 105, N. 7, Abstract No. 60552C, p. 611, Aug. 18, 1986.

*Primary Examiner*—Zinna Northington Davis
*Attorney, Agent, or Firm*—Finnegan, Henderson, Farabow, Garrett & Dunner, L.L.P.

[57] ABSTRACT

Substituted bicyclic heteroaroylguanidines, a process for their preparation, their use as a medicament or a diagnostic agent, and a medicament containing them are described, as are the pharmaceutically tolerated salts thereof. A process for their preparation, and their use as medicines and diagnostic aids in cardiovascular diseases, is also described.

17 Claims, No Drawings

SUBSTITUTED BICYCLIC HETEROAROYLGUANIDINES, A PROCESS FOR THEIR PREPARATION, THEIR USE AS A MEDICAMENT OR A DIAGNOSTIC AGENT, AND A MEDICAMENT CONTAINING THEM

This is a continuation of application Ser. No. 08/968,342, filed Nov. 12, 1997, now abandoned, which is a continuation of application Ser. No. 08/665,580 filed Jun. 18, 1996, now abandoned, which is a continuation of originally filed application Ser. No. 08/434,249, filed May 3, 1995, now abandoned all of which are incorporated herein by reference.

The invention relates to bicyclic heteroaroylguanidines of the formula I

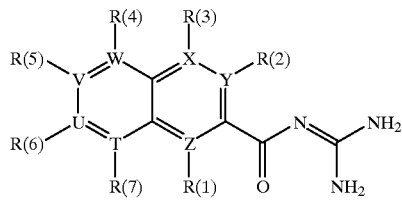

in which:
T, U, V, W, X, Y and Z
are, independently of each other, nitrogen or carbon, with, however, the restriction that X and Z are not nitrogen at the same time,
and that T, U, V, W, X, Y and Z do not carry any substituent when they are nitrogen,
and that not more than four of them are nitrogen at the same time, R(1) and R(2)
are, independently of each other, hydrogen, F, Cl, Br, I, $(C_1-C_3)$-alkyl,
$(C_1-C_3)$-perfluoroalkyl, OR(8), NR(8)R(9) or C(=O)N=C(NH$_2$)$_2$;
R(8) and R(9)
are, independently of each other, hydrogen or $(C_1-C_3)$-alkyl,
or
R(8) and R(9)
are together 4 or 5 methylene groups of which one CH$_2$ group can be replaced by oxygen, S, NH, N—CH$_3$ or N-benzyl, R(3), R(4), R(5), R(6) and R(7)
are, independently of each other, hydrogen, F, Cl, Br, I, —C≡N, $X_k$—(CH$_2$)$_p$—$(C_{q2q+1})$, R(10a)—SO$_{bm}$,
R(10b)R(10c)N—CO, R(11)—CO— or R(12)R(13)N—SO$_2$—,
where the perfluoroalkyl group is straight-chain or branched;
X is oxygen, S or NR(14);
R(14) is H or $(C_1-C_3)$-alkyl;
bm is zero, 1 or 2;
p is zero, 1 or 2;
k is zero or 1;
q is 1, 2, 3, 4, 5 or 6;
R(10a), R(10b), R(11) and R(12)
are, independently of each other,
$(C_1-C_8)$-alkyl, $(C_3-C_6)$-alkenyl,
—$C_nH_{2n}$—R(15) or $(C_1-C_8)$-perfluoroalkyl,
n is zero, 1, 2, 3 or 4;

R(15) is $(C_3-C_7)$-cycloalkyl or phenyl which is not substituted or is substituted by 1–3 substituents selected from the group consisting of F, Cl, CF$_3$, methyl, methoxy and
NR(16)R(17);
R(16) and R(17)
are H or $C_1-C_4$-alkyl;
or
R(10b), R(11) and R(12)
are hydrogen;
R(10c) and R(13)
are, independently, hydrogen or $(C_1-C_4)$-alkyl;
or
R(10b) and R(10c) and also R(12) and R(13)
are together 4 or 5 methylene groups of which one CH$_2$ group can be replaced by oxygen, sulfur, NH, N—CH$_3$ or N-benzyl;
or
R(3), R(4), R(5), R(6) and R(7)
are, independently of each other, $(C_1-C_8)$-alkyl, —$C_{al}H_{2al}$R(18) or $(C_3-C_8)$-alkenyl;
al is zero, 1 or 2;
R(18) is $(C_3-C_8)$-cycloalkyl, phenyl, biphenylyl or naphthyl, where the aromatic systems are not substituted or are substituted by 1–3 substituents selected from the group consisting of F, Cl, CF$_3$, methyl, methoxy and NR(19a)R(19b);
R(19a) and R(19b)
are hydrogen, $(C_1-C_4)$-alkyl or $(C_1-C_4)$-perfluoroalkyl;
or
R(3), R(4), R(5), R(6) and R(7)
are, independently of each other, $(C_1-C_9)$-hetero-aryl which is linked via C or N and which is unsubstituted or substituted by 1–3 substituents from the group consisting of F, Cl, CF$_3$, CE$_3$, methozy, hydroxyl, amino, methylamino or dimethylamino;
or
R(3), R(4), R(5), R(6) and R(7)
are, independently of each other,

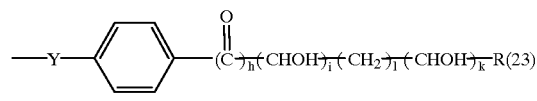

or

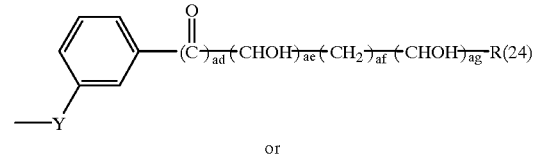

or

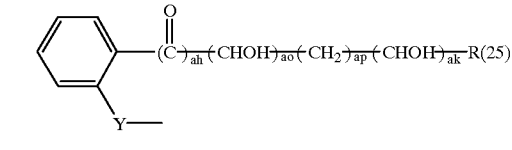

Y is oxygen, —S— or —NR(22)—;
h, ad and ah are, independently of each other, zero or 1;
i, i, k, ae, af, ag, ao, ap and ak are, independently of each other, zero, 1, 2, 3 or 4;
where, however, in each case h, i and k are not zero at the same time, ad, ae and ag are not zero at the same time, and, ah, ao and ak are not zero at the same time, R(23), R(24), R(25) and R(22)
are, independently of each other, hydrogen or $(C_1-C_3)$-alkyl;

or

R(3), R(4), R(5), R(6) and R(7) —are, independently of each other, SR(29),

OR(30), NR(31)R(32) or —CR(33)R(34)R(35); R(29), R(30), R(31) and (33)
are, independently of each other, $—C_aH_{2a}—(C_1-C_9)$-heteroaryl which is substituted by 1–3 substituents selected form the group consisting of F, Cl, $CF_3$, $CH_3$, methoxy, hydroxyl, amino, methylamino and dimethylamino;

a is zero, 1 or 2;

R(32), R(34) and (35)
are, independently of each other, defined as R(29) or hydrogen, $(C_1-C_4)$-alkyl or $(C_1-C_4)$-perfluoroalkyl;

or

R(3), R(4), R(5), R(6) and R(7)
are, independently of each other,

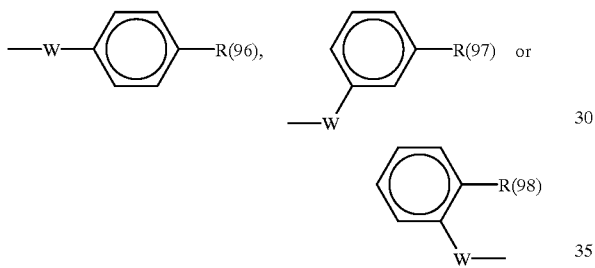

R(96), R(97) and R(98)
are, independently of each other, $(C_1-C_9)$-heteroaryl which is linked via C or N and which is unsubstituted or is substituted by 1 to 3 substituents from the group consisting of F, Cl, $CF_3$, $CH_3$, methoxy, hydroxyl, amino, methylamino, dimethylamino or benzyl;

W is oxygen, B or NR(36)—;

R(36) is H or $(C_1-C_4)$-alkyl;

or

R(3), R(4), R(5), R(6) and R(7)
are, independently of each other, R(46)X(1)—;
X(1) in oxygen, S, NR(47), (D=O)A— or $NR(48)C=MN^{(*)}R(49)$—;
M in oxygen or sulfur;
A is oxygen or NR(50);
D is C or SO;
R(46) is $(C_1-C_8)$-alkyl, $(C_3-C_8)$-alkenyl, $(CH_2)_bC_dF_{2d+1}$ or $—C_xR_{2x}—R(51)$;
b is zero or 1;
d is 1, 2, 3, 4, 5, 6 or 7;
x is zero, 1, 2, 3 or 4;
R(51) is $(C_3-C_8)$-cycloalkyl, phenyl, biphenylyl or naphthyl, where the aromatic systems are not substituted or are substituted by 1–3 substituents selected from the group consisting of F, Cl, $CF_3$, methyl, methoxy and NR(52)R(53);
R(52) and R(53)
are hydrogen, $(C_1-C_4)$-alkyl or $(C_1-C_4)$-perfluoroalkyl;

R(47), R(48) and R(50) are, independently, hydrogen, $(C_1-C_4)$-alkyl or $(C_1-C_4)$-perfluoroalkyl;
R(49) is defined as R(46);

or

R(46) and R(47), or R(46) and R(48), respectively,
are together 4 or 5 methylene groups of which one $CH_2$ group can be replaced by oxygen, sulfur, NH, N—$CE_3$ or N-benzyl;
where A and $N^{(*)}$ are bonded to the phenyl nucleus of the heteroaroylguanidine parent substance;

or

R(3), R(4), R(5), R(6) and R(7)
are, independently of each other, —SR(64), —OR(65), —NHR(66), —NR(67)R(68), —CR(69)R(70), —CR(54)R(55)OH, —C=CR(56), —CR(58)=CR(57) or
—[CR(59)R(60)]$_u$—CO—[CR(61) R(62)]$_v$—R(63);
R(64), R(65), R(66), R(67) and R(69)
are, identically or differently,
—$(CH_2)_y$—(CHON)$_z$—$(CH_2)_{aa}$—(CHOH)$_t$—R(71) or
—$(CH_2)_{AB}$—O—$(CH_2CH_2O)_{ac}$—R(72);
R(71) and R(72) and R(72)
are, independently of each other, hydrogen or methyl;
u is 1, 2, 3 or 4;
v is zero, 1, 2, 3 or 4;
y, z and aa are, identically or differently, zero, 1, 2, 3 or 4;
t is 1, 2, 3 or 4;
R(68), R(70), R(54) and R(55)
are, identically or differently, hydrogen or $(C_1-C_6)$-alkyl;

or

R(69) and R(70), or R(54) and R(55), respectively,
are, together with the carbon atom carrying them, a $(C_3-C_8)$-cycloalkyl;
R(63)
is hydrogen, $(C_1-C_6)$-alkyl, $(C_3-C_8)$-cycloalkyl or —$C_eH_{2e}$—R(73);
e is zero, 1, 2, 3 or 4;
R(56), R(57) and R(73) are, independently, phenyl which is unsubstituted or in substituted by 1–3 substituents selected from the group consisting of F, Cl, $CF_3$, methyl, methoxy and NR(74)R(75);
R(74) and R(75)
are hydrogen or $(C_1-C_4)$-alkyl;

or

R(56), R(57) and R(73) are, independently, $(C_1-C_9)$-heteroaryl which is unsubstituted or is substituted as phenyl;
R(58), R(59), R(60), R(61) and R(62) are hydrogen or methyl;

or

R(3), R(4), R(5), R(6) and R(7)
are, independently of each other, R(76)—NE—$SO_2$—;
R(76) is R(77)R(78)N—(C=Y')—;
Y' is oxygen, S or N—R(79);
R(77) and R(78)
are, identically or differently, hydrogen, $(C_1-C_8)$-alkyl, $(C_3-C_8)$-alkenyl or —$C_fH_{2f}$—R(80);
f is zero, 1, 2, 3 or 4;
R(80) is $(C_5-C_7)$-cycloalkyl or phenyl which is unsubstituted or in substituted by 1–3 substituents selected from the group consisting of F, Cl, $CF_3$, methoxy and $(C_1-C_4)$-alkyl;

or
R(77) and R(78)
   are together 4 or 5 methylene groups of which one CH$_2$ group can be replaced by oxygen, sulfur, NH, N—CH$_3$ or N-benzyl;
R(79) is defined as R(77) or is amidine;
or
R(3), R(4), R(5), R(6) and R(7)
   are, independently of each other, NR(84a)R(85), OR(84b), SR(84c) or —C$_n$H$_{2n}$—R(84d);
   n is zero, 1, 2, 3 or 4;
   R(84d) is (C$_3$–C$_7$)-cycloalkyl or phenyl which is not substituted or is substituted by 1–3 substituents from the group consisting of F, Cl, CF$_3$, methyl, methoxy and NR(16)R(17);
      R(16) and R(17)
         are hydrogen or (C$_1$–C$_4$)-alkyl;
   R(84a), R(84b), R(84c) and R(85)
      are, independently of each other, hydrogen, (C$_1$–C$_8$)-alkyl, (C$_1$–C$_8$)-perfluoroalkyl or (CH$_2$)$_{ax}$—R (84g);
      ax is zero, 1, 2, 3 or 4;
      84g is (C$_3$–C$_7$)-cycloalkyl or phenyl which is not substituted or is substituted by 1–3 substituents selected from the group consisting of F, Cl, CF$_3$, methyl, methoxy and NR(84u)R(84v);
         R(84u) and R(84v) are hydrogen or C$_1$–C$_4$-alkyl;
   or
   R(84a) and R(85)
      are together 4 or 5 methylene groups of which one CH$_2$-group can be replaced by oxygen, sulfur, NH, N-CH$_3$ or N-benzyl,
and the pharmaceutically tolerated salts thereof.
Compounds of the formula I are preferred in which:
T, U, V, W, X, Y and Z
   are, independently of each other, N or C; with, however, the restriction that only one of the positions T, U, V, W, X, Y and Z is nitrogen,
   and that T, U, V, W, X, Y and Z do not carry any substituent when they are nitrogen,
R(1) and R(2)
   are, independently of each other, hydrogen, F, Cl, Br, I, (C$_1$–C$_3$)-alkyl, (C$_1$–C$_3$)-perfluoroalkyl, OR(8) or NR(8)R(9);
   R(8) and R(9) are, independently of each other, hydrogen or (C$_1$–C$_3$)-alkyl;
   or
   R(8) and R(9)
      are together 4 or 5 methylene groups of which one CH$_2$ group can be replaced by oxygen, sulfur, NH, N—CH$_3$ or N-benzyl,
R(3), R(4), R(5), R(6) and R(7)
   are, independently of each other, hydrogen, F, Cl, Br, I, —C≡N, (C$_q$F$_{2q+1}$), R(10a)—SO$_{bm}$, R(10b)R(10c)N—CO, R(11)—CO— or R(12)R(13)N—SO$_2$—,
   where the perfluoroalkyl group is straight-chain or branched;
   bm is 2;
   q is 1, 2, 3, 4, 5 or 6;
   R(10a), R(10b), R(11) and R(12)
      are, independently, (C$_1$–C$_4$)-alkyl, —C$_n$H$_{2n}$—R(15) or (C$_1$–C$_4$)-perfluoroalkyl;
      n is zero, 1 or 2;
      R(15) is (C$_3$–C$_7$)-cycloalkyl or phenyl which is not substituted or is substituted by 1–3 substituents selected from the group consisting of F, Cl, CF$_3$, methyl, methoxy and NR(16)R(17);
         R(16) and R(17)
            are H or CH$_3$;
   or
   R(10b), R(11) and R(12)
      are hydrogen,
   R(10c) and R(13)
      are, independently, hydrogen or (C$_1$–C$_4$)-alkyl;
   or
   R(10b) and R(10c) and also R(12) and R(13)
      are together 4 or 5 methylene groups of which one CH$_2$ group can be replaced by oxygen, sulfur, NH, N—CH$_3$ or N-benzyl,
or
R(3), R(4), R(5), R(6) and R(7)
   are, independently of each other, (C$_1$–C$_8$)-alkyl, —C$_{al}$HK$_{2a}$R(18) or (C$_3$–C$_8$)-alkenyl;
   al is zero, 1 or 2;
   R(18) is (C$_3$–C$_8$)-cycloalkyl or phenyl, where phenyl is not substituted or is substituted by 1–3 substituents selected from the group consisting of F, Cl, CF$_3$, methyl, methoxy and NR(19a)R(19b);
      R(19a) and R(19b)
         are hydrogen, CH$_3$ or CF$_3$;
or
R(3), R(4), R(5), R(6) and R(7)
   are, independently of each other, (C$_1$–C$_9$)-heteroaryl which in linked via C or N and which is unsubstituted or i substituted by 1–3 substituents selected from the group consisting of F, Cl, CF$_3$, CH$_3$, methoxy, hydroxyl, amino, methylamino and dimethylamino;
or
R(3), R(4), R(5), R(6) and R(7)
   are, independently of each other, —Y—[phenyl]—(C)$_h$(CHOH)$_i$(CH$_2$)$_j$(CHOH)$_k$—R(23)

or

[phenyl]—(C)$_{ad}$(CHOH)$_{ae}$(CH$_2$)$_{af}$(CHOH)$_{ag}$—R(24)
—Y or

[phenyl]—(C)$_{ah}$(CHOH)$_{ao}$(CH$_2$)$_{ap}$(CHOH)$_{ak}$—R(25)
Y—

Y is oxygen, —S— or —NR(22)—;
h, ad and ah are, independently of each other, zero or 1;
i j, k, ae, af, ag, ao, ap and ak are, independently of each other zero, 1, 2, 3 or 4,
where, however, in each came h, i and k are not zero at the same time, ad, ae and ag are not zero at the same time, and ah, ao and ak are not zero at the same time, R(23), R(24), R(25) and R(22)
  are, independently, hydrogen or $(C_1-C_3)$-alkyl;
or
R(3), R(4), R(5), R(6) and R(7)
  are, independently of each other, SR(29), —OR(30), —NR(31)R(32) or —CH(33)R(34)R(35);
  —R(29), R(30), R(31) and R(33) are, independently, —$C_aH_{2a}$—($C_1-C_9$)-heteroaryl which in unsubstituted or in substituted by 1–3 substituents selected from the group consisting of F, Cl, $CF_3$, $CH_3$, methoxy, hydroxyl, amino, methylamino and dimethylamino;
  a is zero, 1 or 2,
  R(32), R(34) and R(35)
    are, independently of each other, defined as R(29) or hydrogen, $CH_3$ or CF3;
or
R(3), R(4), R(5), R(6) and R(7)
  are, independently of each other,

 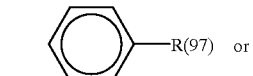 or

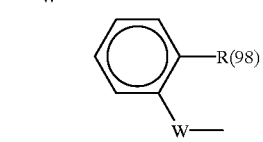

R(96), R(97) and R(98)
  are, independently of each other, $(C_1-C_9)$-heteroaryl which is linked via C or N and which is unsubstituted or is substituted by 1 to 3 substituents from the group consisting of F, Cl, $CF_3$, $CH_3$, methoxy, hydroxyl, amino, methylamino, dimethylamino and benzyl;
  W is oxygen, 5 or NR(36)—;
    R(36) is hydrogen or $(C_1-C_4)$-alkyl;
or
R(3), R(4), R(5), R(6) and R(7)
  are, independently of each other, R(46)X(1)—;
  X(1) is oxygen, sulfur, NR(47), (D=0)A— or NR(48) C=MN$^{(*)}$R(49)—;
  M is oxygen or sulfur;
  A is oxygen or NR(50);
  D is C or SO;
  R(46) is $(C_1-C_8)$-alkyl, $(C_3-C_8)$-alkenyl, $(CH_2)_b$ $C_dF_{2d+1}$, or —$C_xH_{2x}$—R(51);
    b is zero or 1;
    d is 1, 2, 3, 4, 5, 6 or 7;
    x is zero, 1, 2, 3 or 4;
    R(51) is $(C_3-C_8)$-cycloalkyl or phenyl where phenyl is not substituted or is substituted by 1–3 substituents selected from the group consisting of F, Cl, $CF_3$, methyl, methoxy and NR(52)R(53);
      R(52) and R(53) are hydrogen, $CH_3$ or $CF_3$;
    R(47), R(48) and R(50) are, independently, hydrogen, $(C_1-C_4)$-alkyl or $(C_1-C_4)$-perfluoroalkyl;
  R(49) is defined as R(46);
or
  R(46) and R(47), or R(46) and R(48), respectively, are together 4 or 5 methylene groups of which one $CH_2$ group can be replaced by oxygen, sulfur, NH, N—$CH_3$ or N-benzyl;

where A and N$^{(*)}$ are bonded to the phenyl nucleus of the heteroaroylguanidine parent substance;
or
R(3), R(4), R(5), R(6) and R(7)
  are, independently of each other, —SR(64), —OR(65), —NER(66), —NR(67)R(68), —CHR(69)R(70), —CR(54)R(55)OH, —C≡CR(56), —CR(58)=CR (57) or —[CR(59)R60)]$_u$—CO—[CR(61)R(62)]$_v$—R(63);
  R(64), R(65), R(66), R(67) and R(69)
    are, identically or differently,
    —$(CH_2)_y$—$(CHOH)_x$—$(CH_2)_{aa}$—$(CHOH)_t$—R(71) or
    —$(CH_2)_{ab}$—O—$(CH_2-CH_2O)_{ac}$—R(72);
  R(71) and R(72)
    are hydrogen or methyl;
  u is 1, 2, 3 or 4;
  v is zero, 1, 2, 3 or 4;
  y, z and aa are, identically or differently, zero, 1, 2, 3 or 4;
  t is 1, 2, 3 or 4;
  R(68), R(70), R(54) and R(55)
    are, identically or differently hydrogen or $(C_1-C_6)$-alkyl;
or
  R(69) and R(70), or R(54) and R(55), respectively, are, together with the carbon atom carrying them, a $(C_3-C_8)$-cycloalkyl;
  R(63) is hydrogen, $(C_1-C_6)$-alkyl, $(C_3-C_8)$-cycloalkyl or —$C_eH_{2e}$—R(73);
  e is zero, 1, 2, 3 or 4;
  R(56), R(57) and R(73)
    are, independently of each other, phenyl which is unsubstituted or is substituted by 1–3 substituents selected from the group consisting of F, Cl, $CF_3$, methyl, methoxy and NR(74)R(75);
    R(74) and R(75) are hydrogen or $(C_1-C_4)$-alkyl;
  or
  R(56), R(57) and R(73)
    are, independently, $(C_1-C_9)$-heteroaryl which in unsubstituted or is substituted as phenyl,
  R(58), R(59), R(60), R(61) and R(62)
    are hydrogen or methyl;
or
R(3), R(4), R(5), R(6) and R(7)
  are, independently of each other NR(84a)R(85), OR(84b), SR(84c) or —$C_nH_{2n}$—R(84d);
  n is zero or 1;
  R(84d) is $(C_3-C_7)$-cycloalkyl or phenyl which is not substituted or is substituted by 1–3 substituents selected from the group consisting of F, Cl, $CF_3$, methyl, methoxy and NR(16)R(17);
    R(16) and R(17)
      are hydrogen or $CH_3$;
  R(84a), R(84b), R(84c) and R(85)
    are, independently of each other, hydrogen, $(C_1-C_4)$-alkyl, $(C_1-C_4)$-perfluoroalkyl or $(CH_2)_{ax}$—R (84g);
    ax is zero or 1;
    84g is phenyl which is not substituted or is substituted by 1–3 substituents selected from the group consisting of F, Cl, $CF_3$, methyl, methoxy and NR(84u)R(84v);
      R(84u) and R(84v)
        are hydrogen or $(C_1-C_4)$-alkyl;

or
R(84a) and R(85)
  are together 4 or 5 methylene groups of which one CH$_2$ group can be replaced by oxygen, sulfur, NH, N—CH$_3$ or N-benzyl,
and the pharmaceutically tolerated salts thereof.

Compounds of the formula I are particularly preferred in which:

T, U, V, W, X, Y and Z
  are, independently of each other, nitrogen or carbon;
  with, however, the restriction that only one of the positions T, U, V, W, X, Y or Z is nitrogen,
  and
  that T, U, V, W, X, Y and Z do not carry any substituent when they are nitrogen,
  and
  that T, U, V, W, X, Y and Z are not carbon at the same time;
  and
  that R(3), R(4), R(5), R(6) and R(7) are not all hydrogen at the same time when
    a) T, U, V, W, X and Z are carbon and Y is nitrogen,
    or
    b) T, U, V, W, Y and Z are carbon and X is nitrogen;

R(1) and R(2)
  are, independently of each other, hydrogen, F, Cl, Br, I, (C$_1$–C$_3$)-alkyl, (C$_1$–C$_3$)-perfluoroalkyl, OR(8) or NR(8)R(9);
  R(8) and R(9)
    are, independently of each other, hydrogen or (C$_1$–C$_3$)-alkyl;
  or
  R(8) and R(9)
    are together 4 or 5 methylene groups of which one CH$_2$ group can be replaced by oxygen, sulfur, NH, N—C$_3$ or N-benzyl,
or
R(3), R(4), R(5), R(6) and R(7)
  are, independently of each other, hydrogen, F, Cl, Br, I, —C≡N, CF$_3$, CH$_3$SO$_2$ or CH$_3$CO;
or
R(3), R(4), R(5), R(6) and R(7)
  are, independently of each other, (C$_1$–C$_4$)-alkyl or —C$_{al}$H$_{2al}$R(18);
  al is zero or 1;
  R(18) is phenyl which in not substituted or is substituted by 1–3 substituents selected from the group consisting of F, Cl, CF$_3$, methyl, methoxy and NR(19a)R(19b);
  R(19a) and R(19b)
    are H, CH$_3$ or CF$_3$;
or
R(3), R(4), R(5), R(6) and R(7)
  are, independently of each other, (C$_1$–C$_9$)-heteroaryl which is linked via C or N and which is unsubstituted or is substituted by 1–3 substituents selected from the group consisting of F, Cl, CF$_3$, CH$_3$, methoxy, hydroxyl, amino, methylamlno and dimethylamino,
or
R(3), R(4), R(5), R(6) and R(7)
  are, independently of each other, SR(29), —OR(30), —NR(31)R(32) or —CH(33)R(34)R(35);
  R(29), R(30), R(31) and R(33)
    are, independently of each other, —C$_a$H$_{2a}$—(C$_1$–C$_9$)-heteroaryl which is unsubstituted or is substituted by 1–3 substituents selected from the group consisting of F, Cl, CF$_3$, CH$_3$, methoxy, hydroxyl, amino, methylamino and dimethylamino;
  a is zero, 1 or 2;
  R(32), R(34) and R(35)
    are, independently of each other, defined as R(29) or hydrogen, CH$_3$ or CF$_3$;
or
R(3), R(4), R(5), R(6) and R(7)
  are, independently of each other, NR(84a)R(85), OR(84b) or —C$_n$H$_{2n}$—R(84d);
  n is zero or 1;
  R(84d) is phenyl which in not substituted or is substituted by 1–3 substituents selected from the group consisting of F, Cl, CF$_3$, methyl, methoxy and NR(16)R(17);
  R(16) and R(17)
    are hydrogen or CH$_3$;
  R(84a), R(84b) and R(85)
    are, independently of each other, H, (C$_1$–C$_4$)-alkyl, CF3 or (CH$_2$)$_{ax}$—R(84g);
  ax is zero or 1;
  84 g is phenyl which is not substituted or is substituted by 1–3 substituents selected from the group consisting of F, Cl, CF$_3$, methyl, methoxy and NR(84u)R(84v);
    R(84u) and R(84v)
      are hydrogen or CH$_3$;
or
R(84a) and R(85)
  are together 4 or 5 methylene groups of which one CH$_2$ group can be replaced by oxygen, sulfur, NH, N—C$_3$ or N-benzyl,
and the pharmaceutically tolerated salts thereof.

Compounds of the formula I are very particularly preferred in which:

T, U, V, W, Y and Z are carbon;
X is nitrogen;
with, however, the restriction,
  that X does not carry any substituent,
  and
  that R(4), R(5), R(6) and R(7) are not all hydrogen simultaneously;

R(1) and R(2)
  are, independently of each other, hydrogen, F, Cl, CH$_3$, CF$_3$, ON, OCH$_3$ or NH$_2$;
or
R(4), R(5), R(6) and R(7)
  are, independently of each other, hydrogen, F, Cl, Br, I, —C≡N, CF$_3$, CH$_3$SO$_2$ or CH$_3$CO, with the restriction that they are not all hydrogen simultaneously;
or
R(4), R(5), R(6) and R(7)
  are, independently of each other, (C$_1$–C$_4$)-alkyl or —C$_{al}$H$_{2al}$R(18);
  al is zero or 1;
  R(18) is phenyl which is unsubstituted or is substituted by 1–3 substituents selected from the group consisting of F, Cl, CF$_3$, methyl, methoxy and NR(19a)R(19b);
  R(19a) and R(19b)
    are H, CH$_3$ or CF$_3$;
or
R(4), R(5), R(6) and R(7)

are, independently of each other, SR(29) or —OR(30);
R(29) and R(30) are, independently, —$C_aH_{2a}$—($C_1$–$C_9$)-heteroaryl which is unsubstituted or is substituted by 1–3 substituents selected from the group consisting of F, Cl, $CF_3$, $CH_3$, methoxy, hydroxyl, amino, methylamino and dimethylamino;
a is zero or 1;

or

R(4), R(5), R(6) and R(7)
are, independently of each other, NR(84a)R(85), OR(84b) or —$C_nR_{2n}$—R(84d);
n is zero or 1;
R(84d) is phenyl which is unsubstituted or is substituted by 1–3 substituents selected from the group consisting of F, Cl, $CF_3$, methyl, methoxy and NR(16)R(17);
R(16) and R(17)
are hydrogen or $CH_3$;
R(84a), R(84b) and R(85)
are, independently of each other, H, ($C_1$–$C_4$)-alkyl, $CF_3$ or $(CH_2)_{ax}$— R(84g);
ax in zero or 1;
84 g is phenyl which is unsubstituted or is substituted by 1–3 substituents selected from the group consisting of F, Cl, $CF_3$, methyl, methoxy and NR(84u)R(84v);
R(84u) and R(84v)
are hydrogen or $CH_3$;
and the pharmaceutically tolerated salts thereof.

($C_1$–$C_9$)-Heteroaryl is understood to mean, in particular, radicals which are derived from phenyl or naphthyl and in which radicals one or more CH groups are replaced by N and/or in which at least two adjacent CH groups are replaced (with the formation of a five-membered aromatic ring) by S, NE or O. In addition, one or both atoms of the condensation site of bicyclic radicals can (as in indolizinyl) be N atoms.

In particular furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, guinolyl, isoquinolyl, phthalazinyl, quinoxalinyl, cuinazolinyl and cinnolinyl are regarded as heteroaryl.

If one of the substituents R(1) to R(7) contains one or more centers of asymmetry, these can be in either the S or the R configuration. The compounds can be present as optical isomers, as diastereomers, as racemates, or as mixtures thereof.

The designated alkyl radicals and perfluoroalkyl radicals can be either straight-chain or branched.

The invention relates furthermore to a process for preparing the compounds I, wherein compounds of the formula II

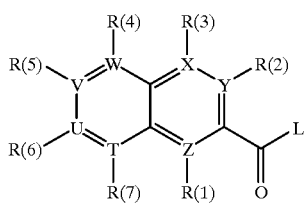

II in which L is a leaving group which can readily be substituted nucleophilically and in which R(1) to R(7) and T, U, V, W, X, Y and Z are defined as above, are reacted with guanidine.

The activated acid derivatives of the formula II, in which L is an alkoxy, preferably a methoxy, group, a phenoxy group, a phenylthio, methylthio or 2-pyridylthio group, or a nitrogen heterocycle, preferably 1-imidazolyl, are advantageously obtained, in a manner known per me, from the underlying carbonyl chlorides (formula II, L=Cl), which, for their part, can be prepared, once again in a manner known per we, from the underlying carboxylic acids (formula II, L=OR), for example using thionyl chloride. In addition to the carbonyl chlorides of the formula II (L=Cl), other activated acid derivatives of the formula II can also be prepared, in a manner known per se, directly from the underlying heteroarylcarboxylic acid derivatives (formula II, L=ON) as can, for example, the methyl enters of the formula II with L=$OCH_3$ by treatment with gaseous HCl in methanol, the imidazolides of the formula XI by treatment with carbonyldiimidazole [L=1-imidazolyl, Staab, Angew. Chem. Int. Ed. Engl. 1,351–367 (1962)], the mixed anhydrides II with Cl—$COOC_2R_5$ or tosyl chloride in the presence of triethylamine in an inert solvent, in addition to which there is also the activation of heteroaryl-carboxylic acids with dicyclohexylcarbodiimide (DCC) or with O-[(cyano(ethoxycarbonyl)methylene)amino]-1,1,3,3-tetramethyluronium tetrafluoroborate ("TOTU") [Proceedings of the 21st European Peptide Symposium, Peptides 1990, Editors E. Giralt and D. Andreu, Escom, Leiden, 1991]. A series of suitable methods for preparing activated carboxylic acid derivatives of the formula II is given, with citation of the source literature, on p. 350 in J. March, Advanced Organic Chemistry, Third Edition (John Wiley a Sons, 1985).

An activated carboxylic acid derivative of the formula II is reacted with guanidine, in a manner known per se, in a protic or aprotic polar, but nevertheless inert, organic solvent. In this context, methanol, isopropanol or THF, between 20° C. and the boiling temperature of these solvents, have proved of value when reacting the methyl heteroarylcarboxylic (II, L=OMe) with guanidine. Most of the reactions of compounds II with malt-free guanidine were advantageously carried out in inert solvents such as THF, dimethoxyethane, dioxane or isopropanol. However, water can also serve as solvent.

When L=Cl, the reaction is advantageously carried out with the addition of an acid capturing agent, for example in the form of excess guanidine, for binding, and thus removing, the hydrohalic acid.

The introduction of substituted sulfur nucleophiles, oxygen nucleophiles or nitrogen nucleophiles is achieved using methods, which are known from the literature, for nucleophilic substitution on an aromatic system. In this substitution, halides and trifluoromethanesulfonates have proved of value as leaving groups. The reaction is advantageously carried out in a dipolar, aprotic solvent, such as, for example, DMF or THU, at a temperature of between 0° C. and the boiling point of the solvent, preferably between 80° C. and the boiling point of the solvent. An alkali metal salt or alkaline earth metal salt having an anion of high basicity and low nucleophilicity, such as, for example, $K_2CO_3$ advantageously serves as the acid-capturing agent.

The introduction of the alkyl or aryl substituents is achieved by the methods, which are )known from the literature, of palladium-mediated cross-coupling of aryl halides with, for example, organozinc compounds, organostannanes, organoboronic acids or organoboranes.

In general, heteroaroylguanidines I are weak bases and can bind acid with the formation of malts. Suitable acid addition salts are the salts of all pharmacologically tolerated acids, for example halides, in particular hydrochlorides, lactates, sulfates, citrates, tartrates, acetates, phosphates, methylsulfonates and p-toluenesulfonates.

The compounds I are substituted acylguanidines. The most prominent representative of the acylguanidines is the pyrazine derivative amiloride which is used in therapy an a potassium-sparing diuretic agent. Numerous further compounds of the amiloride type are described in the literature, such as, for example, dimethyl amiloride or ethyl isopropylamiloride.

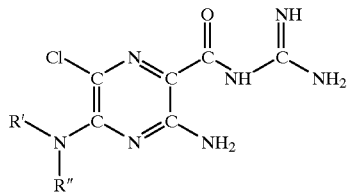

Amiloride: R' and R"=H
Dimethylamiloride: R' and R"=CH$_3$
Ethylisopropylamiloride: R' =C$_2$H$_5$ and R"=CH(CH$_3$)$_2$ In addition to this, investigations have become known which point to amiloride having antiarrhythmic properties (Circulation 79, 1257–63 (1989). However, a factor counting against any widespread use of amiloride an an antiarrhythmic agent is that this effect is only weakly expressed and is accompanied by hypotensive and saluretic effects, which latter side effects are undesirable when treating cardiac arrhythmias.

Indications that amiloride has antiarrhythmia properties were also obtained in experiments on isolated animal hearts [Eur. Heart J. 9 (suppl. 1): 167 (1988) (book of abstracts)]. Thus it was found, using rat hearts, for example, that amiloride was able to completely suppress artificially induced ventricular fibrillation. The abovementioned amiloride derivative ethylisopropyl amiloride was even more potent than amiloride in this model system.

U.S. Pat. No. 5,091,394 (HOE 89/F 288) describes benzoylguanidines which carry a hydrogen atom in the position corresponding to the radical R(1). German Patent Application P 42 04 575.4 (HOE 92/F 034) proposes benzoylguanidines in which, however, the substituents do not have the meanings claimed in accordance with the present invention.

U.S. Pat. No. 3,780,027 claims acylguanidines which are structurally similar to the compounds of the formula I and are derived from loop diuretics, such as bumetanide, which are available commercially. Correspondingly, these compounds are reported to have strong salidiuretic activity.

It was surprising, therefore, that while the compounds according to the invention do not exhibit any undesirable and disadvantageous salidiuretic properties, they do, however, exhibit very good antiarrhythmic properties, as appear, for example, in association with symptoms of oxygen lack. As a consequence of their pharmacological properties, the compounds are outstandingly suitable for use as antiarrhythmic pharmaceuticals possessing a cardioprotective component for the prophylaxis and treatment of infarction and for the treatment of angina pectoris, in connection with which they also inhibit or strongly reduce, in a preventive manner, the pathophysiological processes associated with the genesis of ischemically induced damage, in particular associated with the elicitation of ischemically induced cardiac arrhythmias. On account of their protective effects against pathological hypoxic and ischemic situations, the compounds of the formula I according to the invention can, an a consequence of inhibiting the cellular Na$^+$/R$^+$ exchange mechanism, be used as pharmaceuticals for treating all acute or chronic damage elicited by ischemia, or diseases induced primarily or secondarily thereby. This is the came with regard to their use as pharmaceuticals for surgical interventions, for example in organ transplantations, where the compounds can be used both for protecting the organs in the donor prior to and during removal, for protecting organs which have been removed, for example when they are being treated with or stored in physiological bathing fluids, and when transferring the organs into the recipient. The compounds are likewise valuable protective pharmaceuticals to be used when carrying out angioplastic surgical interventions, for example on the heart or on peripheral vessels. In conformity with their ability to protect against ischemically induced damage, the compounds are also suitable for use as pharmaceuticals for treating ischemias of the nervous system, in particular of the CNS, in connection with which they are suitable, for example, for treating stroke or cerebral edema. Over and above this, the compounds of the formula I according to the invention are also suitable for use in the treatment of forms of shock, such as, for example, allergic, cardiogenic, hypovolemic and bacterial shock.

In addition to this, the compounds of the formula I according to the invention are notable for their strong inhibitory effect on the proliferation of cells, for example the proliferation of fibroblast cells and the proliferation of the smooth muscle cells of the blood vessels. For this reason, the compounds of the formula I are valuable therapeutic agents for use in diseases in which cell proliferation represents a primary or secondary cause and may, therefore, be used as antiatherosclerotic agents, and as agents against diabetic late complications, cancerous diseases, fibrotic diseases such as pulmonary fibrosis, hepatic fibrosis or renal fibrosis, and against organ hypertrophies or hyperplasias, in particular hyperplasia or hypertrophy of the prostate.

The compounds according to the invention are efficient inhibitors of the cellular sodium/proton antiporter (Na$^+$/R$^+$ exchanger), which, in numerous diseases (essential hypertension, atherosclerosis, diabetes, etc.), is also elevated in those cells which are readily accessible to measurement, such as, for example, erythrocytes, thrombocytes or leucocytes. The compounds according to the invention therefore represent outstanding and simple scientific tools, for example in their use am diagnostic aids for defining and differentiating particular forms of hypertension and also of atherosclerosis, diabetes, proliferative diseases, etc. In addition to this, the compounds of the formula I can suitably be used in preventive therapy for preventing the genesis of high blood pressure, for example of essential hypertension.

As compared with the known compounds, the compounds in accordance with the invention exhibit a significantly improved solubility in water. For this reason, they are much more suitable for i.v. administrations.

In this context, pharmaceuticals which contain a compound I may be administered orally, parenterally, intravenously or rectally, or by inhalation, the preferred route of administration depending on the given features of the disease. In this context, the compounds I may be used either alone or together with pharmaceutical auxiliary substances, both in veterinary and in human medicine.

Owing to his specialist knowledge, the person skilled in the art is familiar with those auxiliary substances which are suitable for the desired pharmaceutical formulation. Antioxidants, dispersants, emulsifiers, defoamers, taste corrigents, preservatives, solubilizers or dyes, for example, can be used in addition to solvents, gel formers, suppository bases, tablet auxiliaries and other active compound excipients.

For a form for oral use, the active compounds are mixed with the additives, such as carrier substances, stabilizers or inert diluents, which are suitable for the purpose, and brought by the customary methods into the forms, such as tablets, coated tablets, hard gelatin capsules, or aqueous, alcoholic or oily solutions, which are suitable for administration. Gum arabic, magnesium hydroxide, magnesium carbonate, potassium phosphate, lactose, glucose or starch, in particular corn starch, can, for example, be used as inert excipients. In this context, the preparation can be affected either as a dry granulate or as a wet granulate. Vegetable or animal oils, for example, such as sunflower oil or cod-liver oil, are suitable for use as oily excipients or as solvents.

For subcutaneous or intravenous administration, the active compounds are brought into solution, suspension or emulsion, if desired using the substances, such as solubilizers, emulsifiers or other auxiliary substances, which are customary for the purpose. Examples of suitable solvents are: water, physiological sodium chloride solution or alcohols, for example ethanol, propanol or glycerol, as well as sugar solutions, such as glucose or mannitol solutions, or else a mixture of the different solvents mentioned.

Solutions, suspensions or emulsions of the active compound of the formula I in a pharmaceutically harmless solvent, such as, in particular, ethanol or water, or in a mixture of such solvents, represent examples of suitable pharmaceutical formulations for administration in the form of aerosols or sprays.

An required, the formulation can also contain additional pharmaceutical auxiliary substances such as surfactants, emulsifiers and stabilizers, as well as a propellent gas. Such a preparation customarily contains the active compound in a concentration of from about 0.1 to 10, in particular of from about 0.3 to 3% by weight.

The dosage of the active compound of the formula I to be administered, and the frequency of administration, depend on the strength and duration of the effect of the compounds used; additionally also on the nature and severity of the disease to be treated and on the sex, age, weight and individual responsiveness of the mammalian subject to be treated.

On average, the daily dome of a compound of the formula I is, for a patient of approximately 75 kg in weight, at least 0.001 mg/kg, preferably 0.01 mg/kg, up to at most 10 mg/kg, preferably 1 mg/kg, of body weight. In acute manifestations of the disease, for example immediately after suffering a cardiac infarction, even greater and, in particular, more frequent dosages may also be necessary, for example up to 4 individual doses per day. In the-case of i.v. use in particular, for example in an infarction patient in intensive care, up to 200 mg per day may be necessary.

In this context, pharmaceuticals which contain a compound I may be administered orally, parenterally, intravenously or rectally, or by inhalation, the preferred route of administration depending on the given features of the disease. In this context, the compounds I may be used either alone or together with pharmaceutical auxiliary substances, both in veterinary and in human medicine.

Owing to his specialist knowledge, the person skilled in the art is familiar with those auxiliary substances which are suitable for the desired pharmaceutical formulation. Antioxidants, dispersants, emulsifiers, defoamers, taste corrigents, preservatives, solubilizers or dyes, for example, can be used in addition to solvents, gel formers, suppository bases, tablet auxiliaries and other active compound excipients.

For a form for oral use, the active compounds are mixed with the additives, such an carrier substances, stabilizers or inert diluents, which are suitable for the purpose, and brought by the customary methods into the forms, such as tablets, coated tablets, hard gelatin capsules, or aqueous, alcoholic or oily solutions, which are suitable for administration. Gum arabic, magnesium hydroxide, magnesium carbonate, potassium phosphate, lactose, glucose or starch, in particular corn starch, can, for example, be used as inert excipients. In this context, the preparation can be effected either an a dry granulate or as a wet granulate. Vegetable or animal oils, for example, such as sunflower oil or cod-liver oil, are suitable for use as oily excipients or as solvents.

For subcutaneous or intravenous administration, the active compounds are brought into solution, suspension or emulsion, if desired using the substances, such as solubilizers, emulsifiers or other auxiliary substances, which are customary for the purpose. Examples of suitable solvents are: water, physiological sodium chloride solution or alcohols, for example ethanol, propanol or glycerol, as well as sugar solutions, such as glucose or mannitol solutions, or else a mixture of the different solvents mentioned.

Solutions, suspensions or emulsions of the active compound of the formula I in a pharmaceutically harmless solvent, such as, in particular, ethanol or water, or in a mixture of such solvents, represent examples of suitable pharmaceutical formulations for administration in the form of aerosols or sprays. As required, the formulation can also contain additional pharmaceutical auxiliary substances such as surfactants, emulsifiers and stabilizers, as well as a propellent gas. Such a preparation customarily contains the active compound in a concentration of from about 0.1 to 10, in particular of from about 0.3 to 3% by weight.

The dosage of the active compound of the formula I to be administered, and the frequency of administration, depend on the strength and duration of the effect of the compounds used; additionally also on the nature and severity of the disease to be treated and on the sex, age, weight and individual responsiveness of the mammalian subject to be treated.

On average, the daily dose of a compound of the formula I is, for a patient of approximately 75 kg in weight, at least 0.001 mg, preferably 0.0.01 mg to 10 mg, preferably 1 mg. In acute manifestations of the disease, for example immediately after suffering a cardiac infarction, even greater and, in particular, more frequent dosages may also be necessary, for example up to 4 individual doses per day. In the case of i.v. use in particular, for example in an infarction patient in intensive care, up to 100 mg per day may be necessary.

The novel compounds of the formula I listed below, or their physiologically tolerated salts, can be prepared in analogy with the instructions given in the implementation examples:

List of Abbreviations:

| | |
|---|---|
| MeOH | methanol |
| DMF | N,N-dimethylformamide |
| TMU | N,N,N',N'-tetramethylurea |
| NBS | N-bromosuccinimide |
| AIBN | α,α,-azobis(isobutyronitrile) |
| EI | electron impact |
| DCI | desorption chemical ionization |
| RT | room temperature |
| EA | ethyl acetate (EtOAc) |
| DIP | diisopropyl ether |
| MS | mass spectrum |

| | -continued |
|---|---|
| MTB | methyl tert-butyl ether |
| mp | melting point |
| HEP | n-heptane |
| DME | dimethoxyethane |
| FAB | fast atom bombardment |
| CH₂Cl₂ | dichloromethane |
| THF | tetrahydrofuran |
| eq | equivalent |
| ES | electrospray ionization |
| Me | methyl |
| Et | ethyl |
| Bn | benzyl |
| CNS | central nervous system |
| Brine | saturated aqueous solution of NaCl |

Experimental Section:

General instruction for preparing acylguanidines (I) Variant A: from carboxylic acids (II, L=OR)

1.0 eq. of the carboxylic acid derivative of the formula II is dissolved or suspended in anhydrous THF (5 ml/mmol), and 1.1 eq. of carbonyldiimidazole are then added. After the mixture has been stirred at RT for 2 hours, 5. 0 eq. of guanidine are introduced into the reaction solution. After the mixture has been stirred overnight, the TEF is distilled off under reduced pressure (rotary evaporator), and water is added to the residue, which is then adjusted to from pH 6 to 7 with 2N HCl; the corresponding acylguanidine (formula I) in then filtered off. The acylguanidines obtained in this way can be converted into the corresponding malts by treatment with aqueous, methanolic or ethereal hydrochloric acid or other pharmacologically tolerated acids.

General instructions for preparing acylguanidines (I) Variant B: from alkyl carboxylates (II, L=O-alkyl)

1.0 eq. of the alkyl carboxylate of the formula II and also 5.0 eq. of guanidine (free base) are dissolved in isopropanol or suspended in THF and boiled under reflux until the reaction is complete (monitoring by thin layer chromatography) (typical reaction time, from 2 to 5 h). The solvent is distilled off under reduced pressure (rotary evaporator) and the residue is taken up in EA and washed 3× with a solution of NaHCO₃. Drying takes place over Na₂SO₄, after which the solvent in distilled off in vacuo and the residue is chromatographed on silica gel using a suitable eluent, for example EA/MOH 5:1.

(Salt formation, compare variant A)

EXAMPLE 1

Quinoline-2-carboguanidide Dihydrochloride

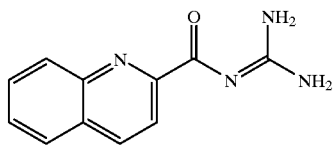

was prepared from quinoline-2-carboxylic acid in accordance with variant A.

MS (ZS): 215 (M+1); mp: >250° C.

EXAMPLE 2

Quinoline-3-carboguanidide Dihydrochloride

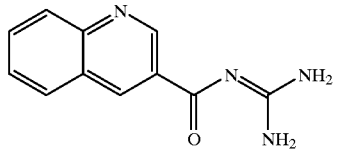

was prepared from quinoline-3-carboxylic acid in accordance with variant A.

MS (ES): 215 (M+1); mp: 217° C.

EXAMPLE 3

Quinolin-6-carboguanidide

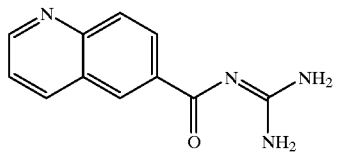

a) 6-Trifluoromethylsulfonyloxyquinoline 1.5 g of 6-hydroxyquinoline are dissolved in 60 ml of $CH_2Cl_2$, and 1.4 ml of 2,6-lutidine, 250 mg of 4-dimethylaminopyridine and 2.0 ml of trifluoromethanesulfonic anhydride are added at −30° C. The mixture is subsequently warmed to RT and then stirred for 1.5 h. The reaction mixture is poured onto 100 ml of saturated aqueous $NaHCO_3$ solution and extracted 3× with 150 ml of ethyl acetate. Drying takes place over $Na_2SO_4$, the solvent is removed in vacuo, and the residue in chromatographed using EA/Rep 2:1. 2.0 g are obtained of a colorless oil.

$R_f$ (NTB)=0.59; MS (DCI): 278 (M+H)⁺ b) Methyl quinoline-6-carboxylate 2.0 g of 6-trifluoromethylsulfonyloxyquinoline are dissolved in 7 ml of MeOH and 14 ml of DMF, and 2.0 ml of triethylamine and also 48 mg of palladium(II) acetate and 88 mg of 1,3-bis(diphenylphomphino)propane are added. The air in the reaction vessel is replaced by CO gas, and the mixture is stirred at 70° C. for 2 h. The mixture is poured into 100 ml of saturated aqueous $RaNCO_3$ solution and extracted 3× with 150 ml of EA. Drying takes place over $Na_2SO_4$, the solvent is removed in vacuo, and the residue is chromatographed using MTB/DIP 1:1. 480 mg are obtained of colorless crystals; mp 86° C.

$R_f$ (MTB)=0.43; MS (DCI):188 (M+H)⁺ c) Quinoline 6-carboguanidide 450 mg of methyl quinoline-6-carboxylate are converted into 410 mg of quinoline 6-carboguanidide in accordance with variant B. mp (dihydrochloride)>270° C.

$R_f$ (EA/MeOH 5:1)=0.13; MS (DCI): 215 (M+H)⁺

EXAMPLE 4

Isoquinoline-6-carboguanidide

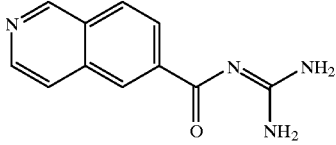

a) Isoquinoline-6-carbaldehyde 1.4 g of 6-methylisoquinoline, 4.0 g of $SeO_2$ and 1.7 g of $K_2CO_3$ are heated to reflux for 7 days in 40 ml of pyridine. The reaction mixture is poured into 100 ml of saturated aqueous $Na_2CO_3$ solution and extracted 3× with 100 ml of EA. Drying takes place over $Na_2SO_4$, the solvent is removed in vacuo, and the residue is chromatographed using MTB. 290 mg are obtained of a colorless oil.

$R_f$ (MTB)=0.28; MS (DCI): 158 (M+H)$^+$ b) Methyl Isoquinoline-6-carboxylate 290 mg of isoquinoline-6-carbaldehyde are dissolved in 40 ml of MeON, and firstly 450 mg of NaCN, then 210 µl of glacial acetic acid, and finally 3.5 g of $MnO_2$ are added. The mixture is stirred at RT for 3 days, and the precipitate is filtered off and the filtrate is poured into a solution of 15 g of $FeSO_4$ in 150 ml of water. Subsequently, the pH of the mixture is adjusted to 9 with $Na_2CO_3$ solution, the precipitate is filtered off, and the filtrate is extracted 3× with 150 ml of EA. Drying takes place over $Na_2SO_4$, and the solvent is removed in vacuo. 190 mg are obtained of a colorless oil, which in reacted without any further purification.

$R_f$ (MTB)=0.40; MS (DCI): 188 (M+H)$^+$ c) Isoquinoline-6-carboguanidide 180 mg of methyl isoquinoline-6-carboxylate are converted into 45 mg of isoquinoline-6-carboguanidide in accordance with variant B.

mp (dihydrochloride)>270° C.

$R_f$ (EA/MeOH 5:1)=0.20; MS (EI): 215 (M+H)$^+$

EXAMPLE 5

2-Naphthoguanidide hydrochloride

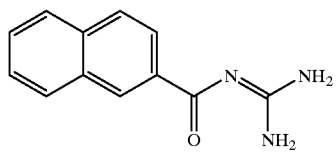

was prepared from naphthalene-2-carboxylic acid in accordance with variant A.

MS (ES): 250 (M+1)

EXAMPLE 6

Isoquinoline-3-carboguanidide

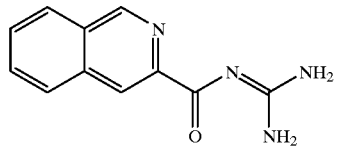

was prepared from isoquinoline-3-carboxylic acid in accordance with variant A.

MS (ES): 215 (M+1) mp: 153° C.

EXAMPLE 7

4-Hydroxy-5,8-difluoroquinoline-3-carboguanidide

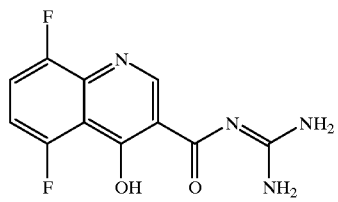

was prepared from the corresponding ethyl ester in accordance with variant B.

MS (ES): 284 (M+1); mp: >230° C.

EXAMPLE 8

6-Chloro-2-methylquinoline-3-carboguanidide hydrochloride

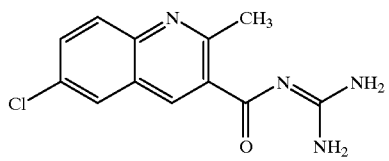

a) Ethyl 6-chloro-2-methylquinoline-3-carboxylate was prepared from 4-chloroaniline and ethyl acetoacetate in accordance with a process known from the literature [David R. Adams, Trina Colman de Saizarbitoria, Synthetic Communications 17 (14), 1647–1653 (1987)].

b) 6-Chloro-2-methylquinoline-3-carboguanidide hydrochloride was prepared from ethyl 6-chloro-2-methylquinoline-3-carboxylate in accordance with variant B.

MS (ES): 263 (M+1); mp: 213° C.

EXAMPLE 9

4-Hydroxy-7-trifluoromethylquinoline-2-carboguanidide hydrochloride

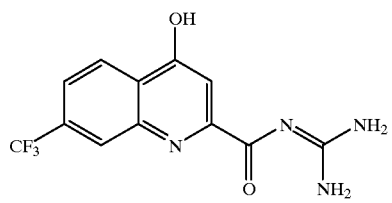

was prepared from 4-hydroxy-7-trifluorome thylquinoline-2-carboxylic ester in accordance with variant B.

MS (ES): 299 (M+1); mp: 142–145° C.

EXAMPLE 10

4,8-Dihydroxyquinoline-3-carboguanidide hydrochloride

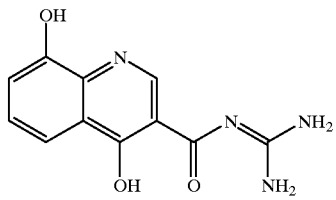

was prepared from 4,8-dihydroxyquinoline-3-carboxylic ester in accordance with variant B.

MS (ES): 247 (M+1); mp: 255–260° C.

Pharmacological data:

Inhibition of the $Na^+/H^+$ exchanger of rabbit erythrocytes:

New Zealand White rabbits (Ivanovas) were given a standard diet containing 2% cholesterol for six weeks in order to activate $Na^+/H^+$ exchange and thus to be able to use flame photometry to determine the $Na^+$ influx into the erythrocytes via $Na^+/R^+$ exchange. The blood was removed from the aural arteries and rendered incoagulable by the addition of 25 IU of potassium heparin. One part of each sample was used for the duplicate determination of the hematocrit by centrifugation. Aliquots of in each case 100 µl were employed for measuring the initial content of $Na^+$ in the erythrocytes.

In order to determine the amiloride-sensitive sodium influx, 100 µl of each blood sample were in each case incubated, at pH 7.4 and 37° C., in 5 ml of a hyperosmolar salt/sucrose medium (mmol/2: 140 NaCl, 3 KCl, 150 sucrose, 0.1 ouabain, 20 tris(hydroxymethyl)aminomethane). The erythrocytes were then washed three times with ice cold $MgCl_2$/ouabain solution (mol/l: 112 $MgCl_2$, 0.1 ouabain) and hemolyzed in 2.0 ml of distilled water. The intracellular content of sodium was determined by flame photometry.

The nett influx of $Na^+$ was calculated from the difference between the initial sodium values and the sodium content of the erythrocytes following incubation. The amilorideinhibitable sodium influx was given by the difference in the sodium content of the erythrocytes following incubation with and without $3 \times 10^{-4}$ mol/l amiloride. The same procedure was also used in the case of the compounds according to the invention.

Results Inhibition of the $Na^+/H^+$ exchanger:

| Example | $IC_{50}$ [µmol/l] |
|---|---|
| 1 | 2–3 |
| 2 | 1.2 |
| 3 | 3–5 |
| 4 | 10 |
| 8 | <1 |

What is claimed is:

1. A bicyclic heteroaroylguanidine of the formula I

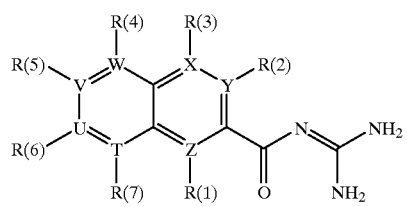

in which:

T, U, V, W, X, Y and Z
are, independently of each other, nitrogen or carbon, with, however, the restriction that only one of the positions T, U, V, W, X, Y or Z is nitrogen, and that T, U, V, W, X, Y and Z do not carry any substituent when they are nitrogen, that T, U, V, W, X, Y and Z are not carbon at the same time; and that R(3), R(4), R(5), R(6) and R(7) are not all hydrogen at the same time when
a) T, U, V, W, X and Z are carbon and Y is nitrogen, or
b) T, U, V, W, Y and Z are carbon and X is nitrogen;

R(1) and R(2)
are, independently of each other, hydrogen, F, Cl, Br, I, $(C_1-C_3)$-alkyl, $(C_1-C_3)$-perfluoroalkyl, OR(8) or NR(8)R(9);

R(8) and R(9)
are, independently of each other, hydrogen or $(C_1-C_3)$-alkyl, or R(8) and R(9)
are together 4 or 5 methylene groups of which one $CH_2$ group can be replaced by oxygen, S, NH, N—$CH_3$ or N-benzyl, R(3), R(4), R(5), R(6) and R(7)
are, independently of each other, hydrogen, F, Cl, Br, I, —C≡N, $CF_3$, $CH_3SO_2$ or $CH_3CO$;

or

R(3), R(4), R(5), R(6) and R(7)
are, independently of each other, $(C_1-C_4)$-alkyl or —$C_{al}H_{2al}$R(18);

al is zero or 1;

R(18) is phenyl, which is not substituted or is substituted by 1–3 substituents selected from the group consisting of F, Cl, $CF_3$, methyl, methoxy and NR(19a)R(19b);

R(19a) and R(19b)
are hydrogen, $CH_3$ or $CF_3$;

or

R(3), R(4), R(5), R(6) and R(7)
are independently of each other, $(C_1-C_9)$-heteroaryl which is linked via C or N and which is unsubstituted

23 or substituted by 1–3 substituents from the group consisting of F, Cl, $CF_3$, $CH_3$, methoxy, hydroxyl, amino, methylamino and dimethylamino;

or

R(3), R(4), R(5), R(6) and R(7)
are, independently of each other, SR(29), —OR(30), —NR(31)R(32) or —R(33)R(34)R(35);
R(29), R(30), R(31) and R(33) are, independently of each other, —$C_aH_{2a}$—$(C_1$–$C_9)$-heteroaryl which is unsubstituted or is substituted by 1–3 substituents selected from the group consisting of F, Cl, $CF_3$, $CH_3$, methoxy, hydroxyl, amino, methylamino and dimethylamino;
a is zero, 1 or 2;
R(32), R(34) and R(35)
are, independently of each other, defined as R(29) or hydrogen, $CH_3$ or $CF_3$;

or

R(3), R(4), R(5), R(6) and R(7)
are, independently of each other, NR(84a)R(85), OR(84 b) or —$C_nH_{2n}$—R(84d);
n is zero or 1;
R(84d) is phenyl which is not substituted or is substituted by 1–3 substituents from the group consisting of F, Cl, $CF_3$, methyl, methoxy and NR(16)R(17);
R(16) and R(17)
are hydrogen or $CH_3$;
R(84a), R(84b) and R(85)
are, independently of each other, hydrogen, $(C_1$–$C_4)$-alkyl,
$CF_3$ or $(CH_2)ax$-R(84g);
ax is zero or 1;
84 g is phenyl which is not substituted or is substituted by 1–3 substituents selected from the group consisting of F, Cl, $CF_3$, methyl, methoxy and NR(84u) and R(84v) are hydrogen or $CH_3$;

or

R(84a) and R(85)
are together 4 or 5 methylene groups of which one $CH_2$-group can be replaced by oxygen, sulfur, NH, N—$CH_3$ or N-benzyl,
or a pharmaceutically tolerated salt thereof.

2. A compound of the formula I as claimed in claim 1, in which:

T, U, V, W, X, Y and Z
are, independently of each other, N or C;
with, however, the restriction that only one of the positions T, U, V, W, X, Y and Z is nitrogen, and that T, U, V, W, X, Y and Z do not carry any substituent when they are nitrogen,
that T, U, V, W, X, Y and Z are not carbon at the same time; and
that R(3), R(4), R(5), R(6) and R(7) are not all hydrogen at the same time when
a) T, U, V, W, X and Z are carbon and Y is nitrogen, or
b) T, U, V, W, Y and Z are carbon and X is nitrogen;
R(1) and R(2)
are, independently of each other, hydrogen, F, Cl, Br, I, $(C_1$–$C_3)$-alkyl, $(C_1$–$C_3)$-perfluoroalkyl, OR(8) or NR(8)R(9);
R(8) and R(9)
are, independently of each other, hydrogen or $(C_1$–$C_3)$-alkyl; or
R(8) and R(9)
are together 4 or 5 methylene groups of which one $CH_2$ group can be replaced by oxygen, sulfur, NH, N-$CH_3$ or N-benzyl,

24

R(3), R(4), R(5), R(6) and R(7)
are, independently of each other, hydrogen, F, Cl, Br, I, —C≡N, $CF_3$, $CH_3SO_2$ or $CH_3CO$; or R(3), R(4), R(5), R(6) and R(7)
are, independently of each other, $C_1$–$C_4$ alkyl, or —$C_aH_{2a}$R(18);
al is zero or 1;
R(18) is phenyl, where phenyl is not substituted or is substituted by 1–3 substituents selected from the group consisting of F, Cl, $CF_3$, methyl, methoxy and NR(19a)R(19b);
R(19a) and R(19b)
are hydrogen, $CH_3$ or $CF_3$; or R(3), R(4), R(5), R(6) and R(7)
are, independently of each other, which is linked via C or N and which is unsubstituted or is substituted by 1–3 substituents selected from the group consisting of F, Cl, $CF_3$, $CH_3$, methoxy, hydroxyl, amino, methylamino and dimethylamino; or R(3), R(4), R(5), R(6) and R(7)
are, independently of each other, SR(29), —OR(30), —NR(31)R(32) or —R(33)R(34)R(35);
R(29), R(30), R(31) and R(33)
are, independently of each other, —$C_aH_{2a}$ —$(C_1$–$C_9)$-heteroaryl which is unsubstituted or is substituted by 1–3 substituents selected from the group consisting of F, Cl, $CF_3$, $CH_3$, methoxy, hydroxyl, amino, methylamino and dimethylamino;
a is zero, 1 or 2;
R(32), R(34) and R(35)
are, independently of each other, defined as R(29) or hydrogen, $CH_3$ or $CF_3$; or R(3), R(4), R(5), R(6) and R(7)
are, independently of each other, NR(84a)R(85), OR(84b) or —$C_nH_{2n}$ —R(84d);
n is zero or 1;
R(84d) is phenyl which is not substituted or is substituted by 1–3 substituents selected from the group consisting of F, Cl, $CF_3$, methyl, methoxy and NR(16)R(17);
R(16) and R(17)
are hydrogen or $CH_3$;
R(84a), R(84b) and R(85)
are, independently of each other, hydrogen, $(C_1$–$C_4)$-alkyl, $CF_3$ or
$(CH_2)_{ax}$—R(84g);
ax is zero or 1;
84g is phenyl which is not substituted or is substituted by 1–3 substituents selected from the group consisting of F, Cl, $CF_3$, methyl, methoxy and NR(84u)R(84v);
R(84u) and R(84v)
are hydrogen or $CH_3$; or
R(84a) and R(85)
are together 4 or 5 methylene groups of which one $CH_2$ group can be replaced by oxygen, sulfur, NH, N—$CH_3$ or N-benzyl.

3. A compound of the formula I as claimed in claim 1, in which:

T, U, V, W, Y and Z are carbon;
X is nitrogen;
with, however, the restriction, that X does not carry any subsitituent, and
that R(4), R(5), R(6) and R(7) are not all hydrogen simultaneously;

R(1) and R(2)
are, independently of each other, hydrogen, F, Cl, $CH_3$, $CF_3$, OH, $OCH_3$ or $NH_2$; or R(4), R(5), R(6) and R(7)
are, independently of each other, hydrogen, F, Cl, Br, I, —C≡N, $CF_3$, $CH_3SO_2$ or $CH_3CO$, with the restriction that they are not all hydrogen simultaneously; or R(4), R(5), R(6) and R(7)
are, independently of each other, $(C_1-C_4)$-alkyl or $-C_{al}H_{2al}R(18)$;
al is zero or 1;
R(18) is phenyl which is unsubstituted or is substituted by 1-3 substituents selected from the group consisting of F, Cl, $CF_3$, methyl, methoxy and NR(19a)R(19b);
R(19a) and R(19b)
are H, $CH_3$ or $CF_3$; or R(4), R(5), R(6) and R(7)
are, independently of each other, SR(29) or —OR(30);
R(29) and R(30)
are independently, $-C_aH_{2a}-(C_1-C_9)$-heteroaryl which is unsubstituted or is substituted by 1-3 substituents selected from the group consisting of F, Cl, $CF_3$, $CH_3$, methoxy, hydroxyl, amino, methylamino and dimethylamino;
a is zero or 1; or R(4), R(5), R(6) and R(7)
are, independently of each other, NR(84a)R(85), OR(84b) or $-C_nH_{2n}-R(84d)$;
n is zero or 1;
R(84d) is phenyl which is unsubstituted or is substituted by 1-3 substituents selected from the group consisting of F, Cl, $CF_3$, methyl, methoxy and NR(16)R(17);
R(16) and R(17)
are hydrogen or $CH_3$;
R(84a), R(84b) and R(85)
are, independently of each other, H, $(C_1-C_4)$-alkyl, $CF_3$ or $(CH_2)_{ax}-R(84g)$;
ax is zero or 1;
84g is phenyl which is unsubstituted or is substituted by 1-3 substituents selected from the group consisting of F, Cl, $CF_3$, methyl, methoxy and NR(84u)R(84v);
R(84u) and R(84v)
are hydrogen or $CH_3$.

4. A process for preparing a compound I as claimed in claim 1, wherein a compound of the formula II

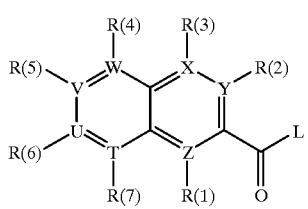

II in which R(1) to R(7) and T, U, V, W, X, Y and Z are defined as in claim 1 and in which L is a leaving group which can readily be substituted nucleophilically, is reacted with guanidine.

5. A method for preparing a pharmaceutical composition for the treatment of arrhythmias, comprising a compound of formula I as claimed in claim 1, wherein said pharmaceutical composition further comprises at least one pharmaceutically acceptable carrier.

6. A method for treating arrhythmias, comprising administering to a patient in need thereof an effective quantity of a compound I as claimed in claim 1.

7. A method for preparing a pharmaceutical composition for the treatment or prophylaxis of cardiac infarction, comprising a compound of formula I as claimed in claim 1, wherein said pharmaceutical composition further comprises at least one pharmaceutically acceptable carrier.

8. A method for preparing a pharmaceutical composition for the treatment or prophylaxis of angina pectoris, comprising a compound of formula I as claimed in claim 1, wherein said pharmaceutical composition further comprises at least one pharmaceutically acceptable carrier.

9. A method for preparing a pharmaceutical composition for the treatment or prophylaxis of ischemic conditions of the heart, comprising a compound of formula I as claimed in claim 1, wherein said pharmaceutical composition further comprises at least one pharmaceutically acceptable carrier.

10. A method for preparing a pharmaceutical composition for the treatment or prophylaxis of ischemic conditions of the peripheral or central nervous system and of stroke, comprising a compound of formula I as claimed in claim 1, wherein said pharmaceutical composition further comprises at least one pharmaceutically acceptable carrier.

11. A method for preparing a pharmaceutical composition for the treatment or prophylaxis of ischemic conditions of peripheral organs and limbs, comprising a compound of formula I as claimed in claim 1, wherein said pharmaceutical composition further comprises at least one pharmaceutically acceptable carrier.

12. A method for preparing a pharmaceutical composition for the treatment of shock conditions, comprising a compound of formula I as claimed in claim 1, wherein said pharmaceutical composition further comprises at least one pharmaceutically acceptable carrier.

13. A method for preparing a pharmaceutical composition for employment in surgical operations and organ transplantations, comprising a compound of formula I as claimed in claim 1, wherein said pharmaceutical composition further comprises at least one pharmaceutically acceptable carrier.

14. A method for preparing a pharmaceutical composition for the preservation and storage of transplants for surgical procedures, comprising a compound of formula I as claimed in claim 1, wherein said pharmaceutical composition further comprises at least one pharmaceutically acceptable carrier.

15. A method for preparing a pharmaceutical composition for the treatment of diseases in which cell proliferation represents a primary or secondary cause, and consequently its use as an antiatherosclerotic agent, or as an agent against diabetic late complications, cancerous diseases, fibrotic diseases which may or may not be pulmonary fibrosis, hepatic fibrosis or renal fibrosis, and hyperplasia of the prostate, comprising a compound of formula I as claimed in claim 1, wherein said pharmaceutical composition further comprises at least one pharmaceutically acceptable carrier.

16. A method for diagnosing hypertension and proliferative diseases by inhibiting the $Na^+/H^+$ exchanger through administering a compound of formula I as claimed in claim 1 to said subject.

17. A pharmaceutical composition, said composition comprising an effective amount of at least one compound of the formula I as claimed in claim 1, together with a pharmaceutically acceptable carrier.

* * * * *

UNITED STATES PATENT AND TRADEMARK OFFICE
CERTIFICATE OF CORRECTION

PATENT NO.    : 6,093,729
DATED         : July 25, 2000
INVENTOR(S)   : Schwark et al.

It is certified that error appears in the above-identified patent and that said Letters Patent is hereby corrected as shown below:

Claim 1, column 23,
Line 7, "–R(33)R(34)R(35)" should read -- –CR(33)R(34)R(35) --.

Claim 2, column 24,
Line 15, before "which", insert -- ($C_1$–$C_9$)-heteroaryl --.
Line 22, "–R(33)R(34)R(35)" should read -- –CR(33)R(34)R(35) --.

Claim 3, column 24,
Line 65, "subsitituent" should read -- substituent --.

Signed and Sealed this

Thirtieth Day of October, 2001

Attest:

NICHOLAS P. GODICI
Attesting Officer
Acting Director of the United States Patent and Trademark Office